United States Patent [19]

Lawless

[11] Patent Number: 4,547,277

[45] Date of Patent: * Oct. 15, 1985

[54] OXYGEN-SEPARATOR

[76] Inventor: William N. Lawless, c/o CeramPhysics, Inc., P.O. Box 346, Westerville, Ohio 43081

[*] Notice: The portion of the term of this patent subsequent to Jul. 31, 2001 has been disclaimed.

[21] Appl. No.: 628,381

[22] Filed: Jul. 12, 1984

Related U.S. Application Data

[63] Continuation-in-part of Ser. No. 464,248, Feb. 7, 1983, Pat. No. 4,462,891.

[51] Int. Cl.$^4$ ............................................. C25B 13/04
[52] U.S. Cl. .................... 204/252; 204/253; 204/295; 204/283
[58] Field of Search ............ 55/2, 143, 145, 146, 55/16, 158; 204/421, 412, 426, 424, 427, 267, 242, 252, 295, 283, 253; 429/30, 32, 33, 191, 193; 501/134, 136, 152

[56] References Cited

U.S. PATENT DOCUMENTS 4,207,159 6/1980 Kimura et al. .................... 204/425
4,304,652 12/1981 Chiba et al. ...................... 204/425
4,462,891 7/1984 Lawless ........................... 429/33 X

*Primary Examiner*—Andrew H. Metz
*Assistant Examiner*—Nam X. Nguyen
*Attorney, Agent, or Firm*—Killworth, Gottman, Hagan, and Schaef

[57] ABSTRACT

Oxygen ion conducting ceramic materials are disclosed, represented by the formulas $$Ni(Nb_{1-x}M_x)_2O_{6-x} \text{ and } Ni_2(Nb_{1-x}M_x)_2O_{7-x}.$$

wherein M is selected from the group consisting of $Zr^{+4}$, $Ti^{+4}$, $Sn^{+4}$, $Sm^{+4}$, $Hf^{+4}$ and $Ce^{+4}$ and x is a value from 0 to 0.2. These materials, along with $Bi_2O_3$ in solid solution with $Y_2O_3$ or $Nb_2O_5$, may be used in an oxygen separator for removing oxygen from a first gas to a second gas or vacuum. The oxygen separator includes at least one layer of the ceramic material with layers of a porous metallic conductor arranged on either side to form a body. An electrode connects one layer, and a second electrode connects the opposite metallic layer. A voltage signal is applied across the electrodes, whereupon oxygen ions diffuse through the ceramic layer.

7 Claims, 7 Drawing Figures

OXYGEN SEPARATOR

RELATED APPLICATION

This application is a continuation-in-part of Ser. No. 464,248, filed Feb. 7, 1983, now U.S. Pat. No. 4,462,891.

BACKGROUND OF THE INVENTION

The present invention relates to an oxygen separator, and more particularly, to such a device for separating oxygen from a first gas having a relatively high oxygen partial pressure into a vacuum or a second gas having a relatively low oxygen partial pressure.

Oxygen sensing devices are generally well known. One common type of presently known sensing device functions by monitoring the EMF developed across an oxygen ion conductor which is exposed to gases having different partial pressures of oxygen.

Oxygen tends to move from a gas containing a high concentration of oxygen to one of lower concentration. If the two gases are separated from each other by an oxygen ion conductor, the oxygen molecules will dissociate on one surface of the conductor and absorb electrons to form oxygen ions. These ions can then diffuse through the ionic conductor, leaving the entry surface with a deficiency of electrons. On the exit or low oxygen concentration side of the conductor, oxygen ions leaving the material must give up electrons to form molecular oxygen, leaving the exit surface with an excess of electrons. Thus, an electrical potential difference, or EMF, is set up between the two surfaces of the ion conductor. The greater the difference in oxygen content of the two gases, the greater will be the tendency of oxygen to diffuse through the conductor, and the greater will be potential difference between the entry and exit surfaces.

The EMF generated by the difference in partial pressures may be calculated by the Nernst relation:

$$EMF = t_i(RT/nF) \ln (P_{O2}/P'_{O2}).  \quad (1)$$

where $t_i$ is the ionic transference number, R is the gas constant, T is the absolute temperature, n is the number of electrons involved in the electrode reaction, F is the Farady constant, and $P_{O2}$ and $P'_{O2}$ are the oxygen partial pressures in the first and second gases, respectively. In the present case, the electrode reaction is $O_2 + 4e \rightarrow 2O^{-2}$, and thus n=4.

The basic principles underlying operation of an oxygen separator stem from the same principles responsible for the functioning of the oxygen sensor, and demonstrate the reciprocity principle of physics. If an oxygen ion conducting material separates two gases with different oxygen partial pressures $P_{O2}$ and $P'_{O2}$, then a voltage signal will appear across the material due to the diffusion of oxygen ions thereacross. The ions diffuse through the material to equalize the partial pressures, and a basic oxygen sensor is the result. However, if a voltage is applied to the oxygen ion conducting material, and if $P_{O2} = P'_{O2}$, the oxygen ions will be forced to flow across the material such that $P_{O2} \neq P'_{O2}$. Thus, one gas will become richer in oxygen than the other, resulting in a basic oxygen separator.

As an alternative way of viewing the operation of an oxygen separator, consider an oxygen sensor in which a certain voltage signal V is generated by two gases in which $P_{O2} \neq P'_{O2}$. Now, if a reverse voltage $-V$ is applied to the material, the flow of oxygen ions through the material will be completely stopped. Increasing the magnitude of the negative voltage will then cause oxygen ions to flow in a reverse direction.

Consequently, an oxygen separator can be formed by operating an oxygen sensor in reverse. What is needed, therefore, is a physical structure for such a separator that can provide a practical application of these principles.

SUMMARY OF THE INVENTION

The present invention meets this need by providing an oxygen separator generally of the oxygen ion conducting type. The ceramic materials used in the separator may be represented by the following formulas:

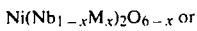

where M is selected from the group consisting of $Zr^{+4}$, $Ti^{+4}$, $Sn^{+4}$, $Sm^{+4}$, $Hf^{+4}$, $Ce^{+4}$ and mixtures thereof, and where x is a value from 0 to 0.2. Additionally, the ceramic material may be $Bi_2O_3$ in solid solution with either $Y_2O_3$ or $Nb_2O_5$.

A preferred electrolytic ceramic material for use in the separator is $NiNb_2O_6$, which may be produced by mixing $Nb_2O_5$ and NiO in appropriate amounts. The mixture is then calcined for approximately two hours at 1000° C., and sintered for approximately one hour at 1350° C. However, all of the above ceramic materials are useful in the practice of the present invention.

Such a separator, for determining the oxygen partial pressure of a first gas relative to the oxygen partial pressure of a second, reference gas, includes at least two layers of a porous metallic conductor. A layer of the ceramic material of the present invention is disposed between the metallic layers to form at least a portion of a solid body for the separator. Individual electrodes are connected to each of the metallic layers, and the separator is located relative to the gases so that one layer is exposed to the first gas, and the second layer is exposed to the second, reference gas. The porous metallic layers may be made of platinum or other suitable metal.

Accordingly, it is an object of the present invention to provide an oxygen ion conducting oxygen separator constructed of a new electrolytic ceramic material; to provide such a separator including a layer of an electrolytic ceramic material between layers of a porous metallic material; to provide such a separator having reduced material and production costs relative to presently known separators; to provide such a separator having a high degree of thermal shock resistance; and to provide such a separator that is simple and can be made of relatively small size.

Other objects and advantages of the invention will be apparent from the following description, the accompanying drawings and the appended claims.

DETAILED DESCRIPTION OF THE PREFERRED EMBODIMENTS

A preferred oxygen ion conducting ceramic material for use in the practice of the present invention is $NiNb_2O_6$. It has been found that $NiNb_2O_6$ can be formed as a dense ceramic body by mixing $Nb_2O_5$ and NiO, calcining for 1 to 3 hours at 800° C. to 1000° C., preferably two hours at 1000° C., and sintering for 1 to 30 hours at 1200° C. to 1400° C., preferably one hour at 1350° C. A ratio of 78.07% $Nb_2O_5$ to 21.93% NiO by weight is preferred. Under the preferred conditions, the ceramic sinters with no weight loss or gain to a density of 97.2% of the theoretical density of 5.653 gm/cm³. A higher percentage of the theoretical density may be achieved using one of several methods well known in the ceramic art including, for example, a longer sintering time, finer starting particle size or hot-pressing.

Figure 3:
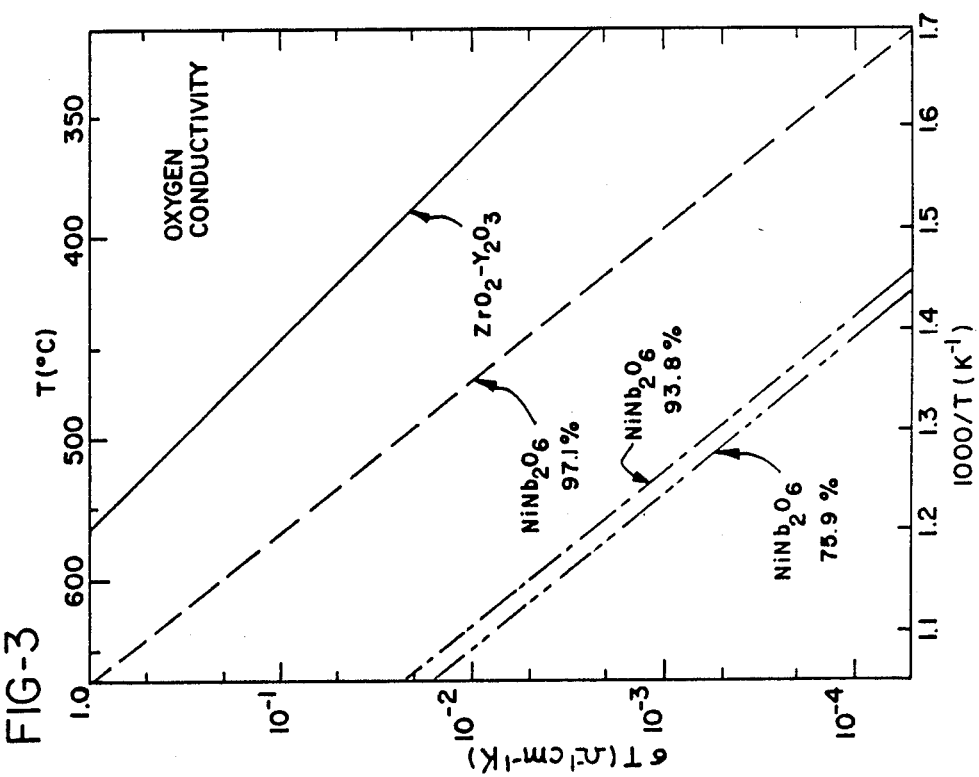
FIG. 3 is a graphical representation of the ionic conductivity of $NiNb_2O_6$ at several densities and of $ZrO_2 + 8\% Y_2O_3$ as a function of temperature.

Ionic conductivity measurements made on three bar samples of the $NiNb_2O_6$ ceramic material at three different densities and on a portion of a densified $ZrO_2$ plus 8% $Y_2O_3$ ceramic tube were used to obtain the data shown in FIG. 3. These data are plotted according to the ionic conductivity relation $$\sigma T = A \exp(-Q/kT) \quad (2)$$

where $\sigma$ is the ionic conductivity, A is a constant, Q is the activation energy, and k is Boltzman's constant. The FIG. 3 data show that the ionic conductivity of $NiNb_2O_6$ increases very rapidly with increasing density and approaches the conductivity of $ZrO_2:Y_2O_3$.

The FIG. 3 data were fitted to the ionic conductivity relation set out as Eq. (2) above, and the resulting fitting parameters are given in Table I.

TABLE I

| Material | Ionic Conductivity Parameters | |
|---|---|---|
| | Ln A | Q (ev) |
| $NiNb_2O_6$, 75.4% theo. density | 12.31 | 1.27 |
| $NiNb_2O_6$, 93.8% theo. density | 11.87 | 1.28 |
| $NiNb_2O_6$, 97.1% theo. density | 15.38 | 1.31 |
| $ZrO_2$ + 8% $Y_2O_3$ | 14.30 | 1.03 |

For $ZrO_2:Y_2O_3$, the activation energy in Table I and $\sigma$-values from FIG. 3, agree well with published data. For $NiNb_2O_6$, the Table I data show that the rapid increase in $\sigma$ with density is primarily due to the rapid increase of ln A with density.

X-ray analysis of $NiNb_2O_6$ has shown that the ceramic is a single-phase, columbite structure. Consequently, it is believed that the oxygen ion conductivity is due to the oxygen vacancies in the columbite structure. The columbite structure, $AB_2O_6$ (where A and B are metal cations and O is oxygen), is obtained from the pyrochlore structure, $A_2B_2O_7$, by the removal of layers A and O ions. In turn, the pyrochlore structure has an eighth layer of oxygen ions missing in comparison to the $A_4O_8$ fluorite structure, which has no oxygen vacancies. It will be noted that $ZrO_2$ and $CeO_2$ have the fluorite structure, and oxygen vacancies for ion conductivity must be produced by dopants such as CaO or $Y_2O_3$. No such such dopants are necessary in the case of $NiNb_2O_6$.

Other ceramic materials useful in the practice of the present invention include two families of ceramics, one being the columbite structure exemplified by $NiNb_2O_6$, and the second being the pyrochlore structure exemplified by $Ni_2Nb_2O_7$. These materials are represented by the following formulas:

$$Ni(Nb_{1-x}M_x)_2O_{6-x} \text{ and}$$

$$Ni_2(Nb_{1-x}M_x)_2O_{7-x}.$$

where M may be $Zr^{+4}$, $Ti^{+4}$, $Sn^{+4}$, $Sm^{+4}$, $Hf^{+4}$ or $Ce^{+4}$, and where x is a value from 0 to 0.2. It is noted that ionic radii considerations favor $Ti^{+4}$, $Sm^{+4}$, $Hf^{+4}$ and $Zr^{+4}$. Some of these materials may have higher ionic conductivities than $NiNb_2O_6$.

Thermal conductivity measurements performed at room temperature on a sample of the $NiNb_2O_6$ ceramic material at approximately 97% of theoretical density indicate a very large value, 0.036 cal sec$^{-1}$ cm$^{-1}$ K$^{-1}$. By way of comparison, this thermal conductivity is approximately 60% of the alumina value at room temperature which, as is well known, has one of the largest room-temperature thermal conductivities of any known non-metal.

The thermal expansion coefficient of the $NiNb_2O_6$ ceramic is $48 \times 10^{-7}$ K$^{-1}$ at room temperature. This moderate thermal expansion coefficient combined with the large thermal conductivity value ensures thermal-shock resistance for this ceramic.

Because of the convenient sintering temperatures of the ceramic materials of the present invention (approximately 1350° C.), the ceramics can be "tape cast" into a monolithic body. As is well known in the ceramic art, tape casting is a process for making a multi-layered body (for example, a ceramic capacitor) wherein appropriate metal electrodes are interdispersed between the ceramic layers.

Figure 1:
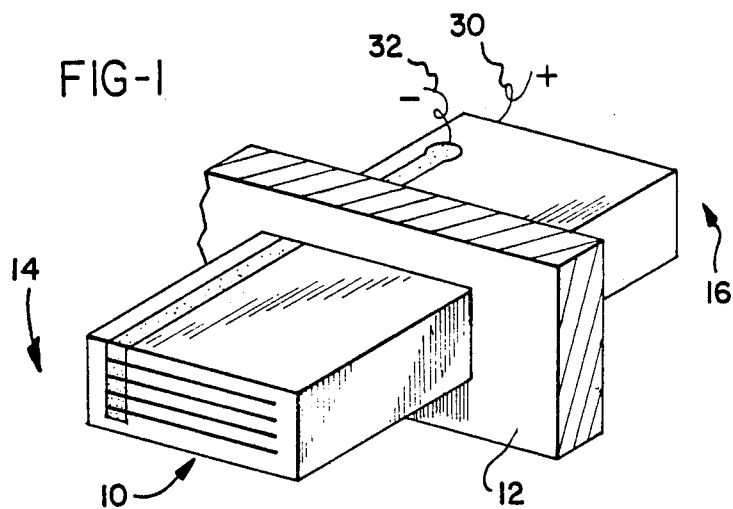
FIG. 1 is a perspective view of a multi-layer device according to the present invention, useful as an oxygen separator.
Figure 2:
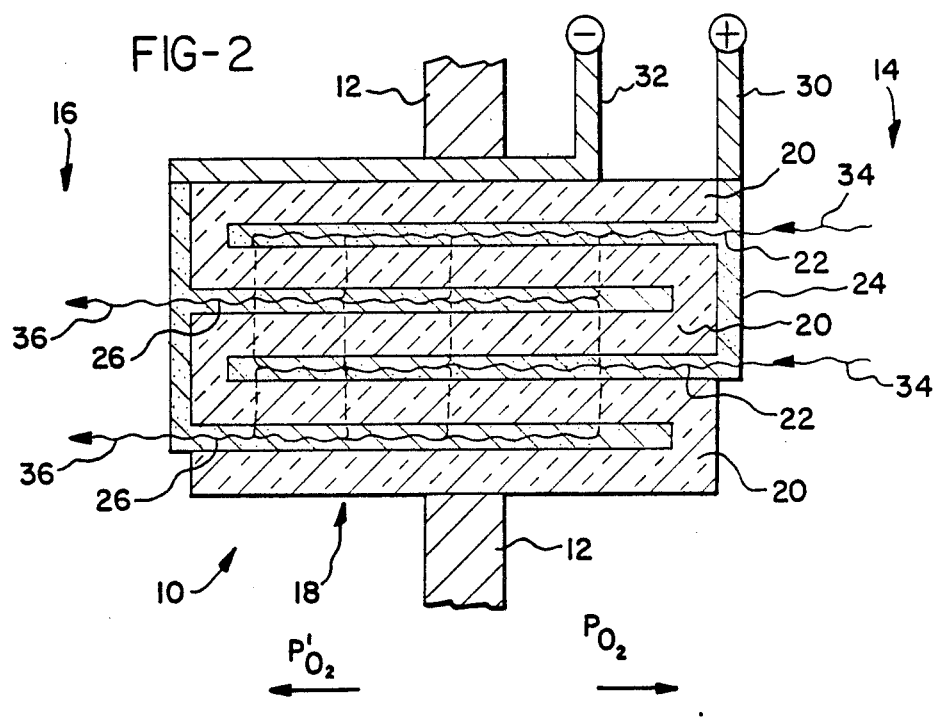
FIG. 2 is a schematic representation of the device of FIG. 1.

A schematic representation of an oxygen sensor (which is a reversed oxygen separator, and vice versa) constructed according to tape-casting methods is shown in FIGS. 1 and 2. As seen in FIG. 2, an oxygen sensor 10 is shown mounted through a baffle 12 disposed so as to maintain a first gas having an oxygen partial pressure $P_{O2}$ on the side of baffle 12 indicated generally at 14. A second gas having an oxygen partial pressure $P'_{O2}$ less than that of the first gas is maintained on the side of baffle 12 indicated generally at 16. The sensor 10 includes a body 18 formed of alternating layers 20 of an electrolytic ceramic material and porous layers of a metallic material. Of the metallic layers, alternate layers 22 extend to a first side 24 of body 18 where they are exposed to the first gas at 14. The remaining metallic layers 26 are exposed along a second, opposing side 28 of body 18 to the second gas at 16. An electrode 30 is connected to the metallic layers 22, while an electrode 32 is connected to metallic layers 26.

The metallic layers 22 and 26 are preferably of platinum, although they may be constructed of any suitable metallic catalytic metal material. The layers 22 and 26 are fine-grained to avoid irreversible electrode effects, and are sponge-like to permit very rapid oxygen transport within the electrode layers. The oxygen contained within the first and second gases diffuses into the metallic layers as indicated by arrows 34, and thus the oxygen concentration within layers 22 corresponds to the concentration within the first gas, and the oxygen concentration within layers 26 corresponds to that of the second gas. Consequently, the oxygen ion concentrations at any two opposing metallic layers are different, and an EMF is developed by the oxygen ions diffusing across the separated ceramic layers 20. The gaseous oxygen resulting in metallic layers 26 then diffuses into the second gas along the path shown by arrows 36.

In essence, therefore, the oxygen sensor 10 consists of N galvanic cells connected in parallel, where N is the number of ceramic layers. The voltage output signal across electrodes 30 and 32 may be calculated through use of the Nernst equation set out above as Eq. (1).

Since an oxygen sensor and an oxygen separator are essentially the same device, the multi-layer geometry described in connection with a sensor may also be used for an oxygen separator. This geometry is preferred for an oxygen sensor, and also represents the best mode presently contemplated for an oxygen separator. In particular, the advantages of such a geometry include ease of construction by a tape-casting technique (to be described in detail below), and the ability of such a geometry to produce a device that is relatively compact in physical size while presently a substantial surface area of the ceramic material for ion diffusion. It should be recognized, however, that in order to achieve large throughputs, it may turn out that the exposed outer surface area could be sufficiently important that other geometries for the separator may ultimately prove to be more desirable. For example, the separator could be constructed in the form of a tube or manifold.

Due to the temperature dependence of the Nernst relationship, it will be seen that some means for determining the temperature of the oxygen separator must be provided to control the voltage signal input into the separator properly. This may be accomplished, for example, either by using standard thermocouple methods or by silk-screening a $Pt+Pt-20\% \ Rh$ thermocouple joint directly into the multi-layered device.

A multi-layer separator is preferably constructed by a tape-casting technique. A powdered electrolytic ceramic material of approximately one micron grain size is mixed with an appropriate organic binder and prepared into a film sheet, preferably of 0.003 inch (0.0075 cm) thickness. A platinum layer is silk-screened onto the sheet, and a predetermined number of such sheets are stacked. The stack is heated at 250° C. to 400° C. for 2 to 30 hours, preferably 290° C. for 28 hours, so as to completely burn out the binder material. At the same time, pressure of 0 to 200 psi is applied to the stack to aid in holding it together. The heating of the stack is then increased, preferably at approximately 150° C. per hour, to a final temperature of 1200° C. to 1400° C. (preferably 1320° C.), at which the stack is held for 30 minutes to 3 hours at an applied pressure of 0 to 5000 psi.

One major criterion of either an oxygen sensor or separator is the threshold operating temperature, defined for a sensor as that temperature to which the device must be heated so that the internal resistance of the oxygen sensor is sufficiently below the external load resistance that the sensor output signal can be processed. For $ZrO_2$ plus 8% $Y_2O_3$, the threshold operating temperature is approximately 600° C.

For the multi-layer sensor device disclosed herein, the total internal resistance $R_t$ is $$R_t = R_c/N = d/NA\sigma \tag{3}$$

where $R_c$ is the resistance of one layer of thickness d and metallic layer area A, $\sigma$ is the ionic conductivity of the $NiNb_2O_6$ ceramic, and N is the number of ceramic layers in the device. The threshold operating temperature for the multi-layer $NiNb_2O_6$ device may be estimated, given that 600° L C. is the threshold for a $ZrO_2+8\%$ $Y_2O_3$ tube, by solving $$(R_t)_{ZrO_2} = (R_t)_{NiNb_2O_6} \tag{4}$$

The typical dimensions of a known zirconia tube oxygen sensor (i.e., approximate diameter of ⅜ inch, wall thickness of 0.05 inches, and length of 6 inches), and the preferred thickness (0.002 inches) and an exemplary surface area (0.025 sq. inches) of the disclosed device are used. Additionally, the data of Table I allow estimation of ln A and Q as a function of density $\sigma$ by making the reasonable assumption that $\ln A \propto \rho$ and $Q \propto \rho$ for $\rho > 90\%$ of theoretical density.

Figure 4:
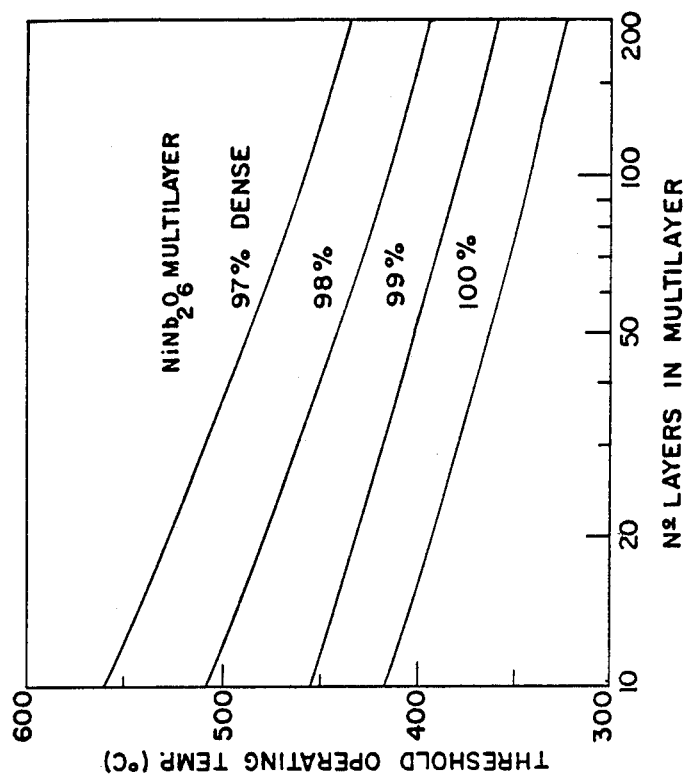
FIG. 4 is a graphical representation of initial operating temperature of multi-layer devices constructed of $NiNb_2O_6$ at one of several densities as a function of the number of layers of $NiNb_2O_6$.

The results of these calculations are shown graphically in FIG. 4 where the temperature is estimated as a function of the number of layers N. Up to the maximum 200 layers shown in FIG. 4 is consistent with state of the art tape casting methods. The graphical representations illustrate that the $NiNb_2O_6$ multi-layer oxygen sensing device can have a significantly lower threshold operating temperature than the presently known zirconia tubes, particularly at higher ceramic densities.

It will be noted that these estimates are not particularly sensitive to the tube or multi-layer device dimensions used, and the latter dimensions are intended to be illustrative rather than restrictive. Additionally, any increased ionic conductivity for the device through the use of the alternative materials disclosed herein will result in further lowering of the threshold operating temperature of the device.

These concerns are of equal, if not greater importance with an oxygen separator of the type described herein. Since certain threshold operating temperatures exist for various embodiments of the device, it will be necessary to operate the device in a heated environment. Thus, selection of the particular embodiment for the device will depend to some extent upon the availability of such an environment.

Figure 6:
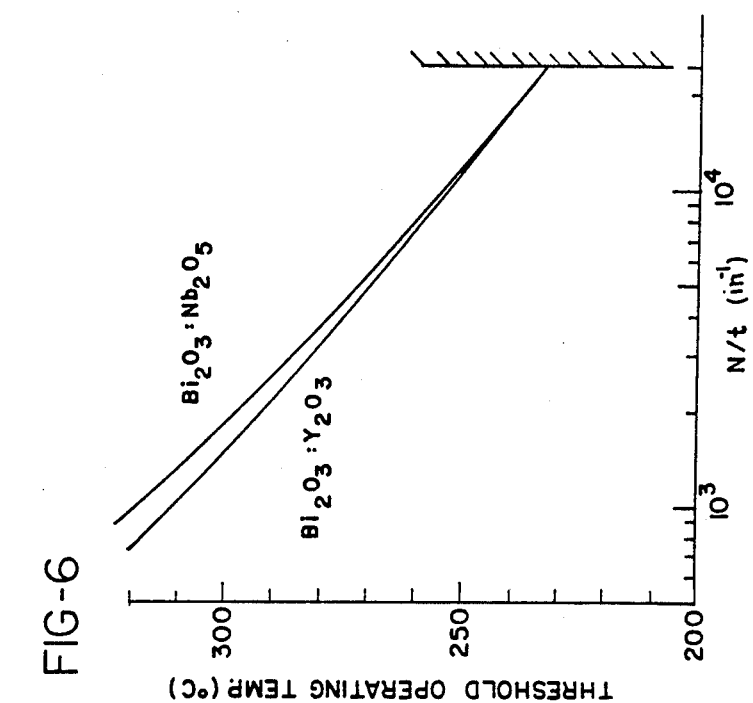
FIG. 6 is a graphical representation of initial operating temperature of multi-layer devices constructed of $Bi_2O_3:Y_2O_3$ and $Bi_2O_3:Nb_2O_5$ as a function of the number of ceramic layers in the device.
Figure 5:
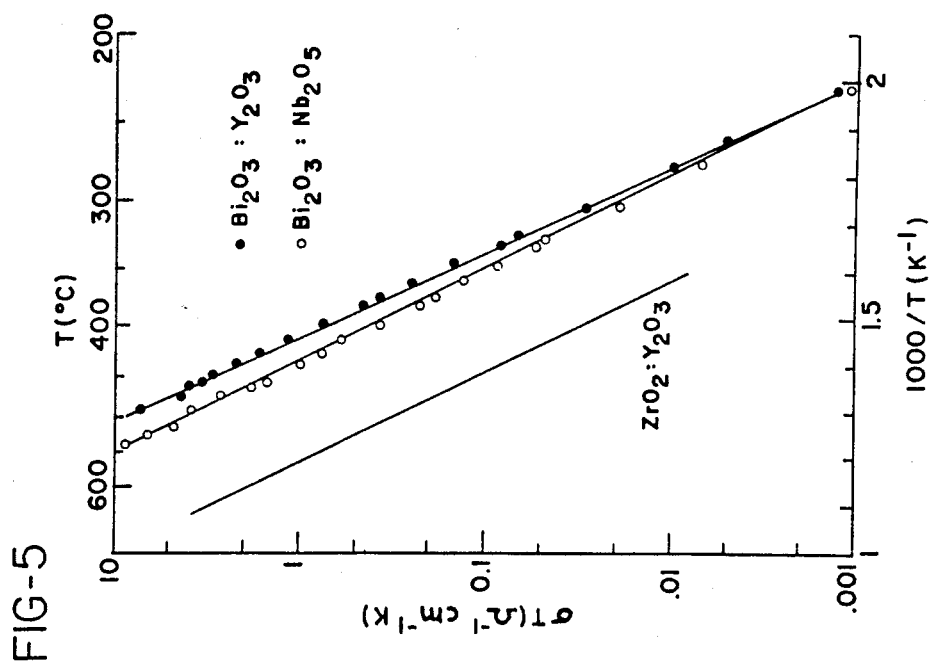
FIG. 5 is a graphical representation of the ionic conductivity of $Bi_2O_3:Y_2O_3$, $Bi_2O_3: Nb_2O_5$ and $ZrO_2:Y_2O_3$ as a function of temperature.

It will be recognized, of course, that while the above calculations concern the $NiNb_2O_6$ multi-layer device, the design and construction techniques of the device may be used with any of the new ceramic materials disclosed herein. In addition, however, it has been found that $Bi_2O_3$ in solid-solution with either $Y_2O_3$ or $Nb_2O_5$ has an oxygen conductivity considerably larger than either $NiNb_2O_6$ or $ZrO_2:Y_2O_3$. Oxygen conductivity data on these materials similar to that shown in FIG. 3 is presented in FIG. 5. These $Bi_2O_3$ ceramics also have sintering temperatures low enough to permit their use with the multi-layer tape casting method described herein. Further, the threshold operating temperatures for devices constructed from these materials, calculated in the same manner as those presented in FIG. 4, are shown in FIG. 6.

Finally, it will be noted that due to the configuration of the device, the corrosion and/or erosion of the metallic layers in the multi-layer device will be considerably reduced compared to the tube devices. If necessary, however, overcoating of the exposed metallic layers with a protective, porous spinel will maintain the life of the device. Moreover, the relatively small size of the multi-layer device will allow for the addition of special exhaust-gas filtering and/or purification catalytic devices to protect the sensor. At the same time, the size of the device may be selected so that it is compatible with the fixture geometries currently used with zirconia tubes.

Figure 7:
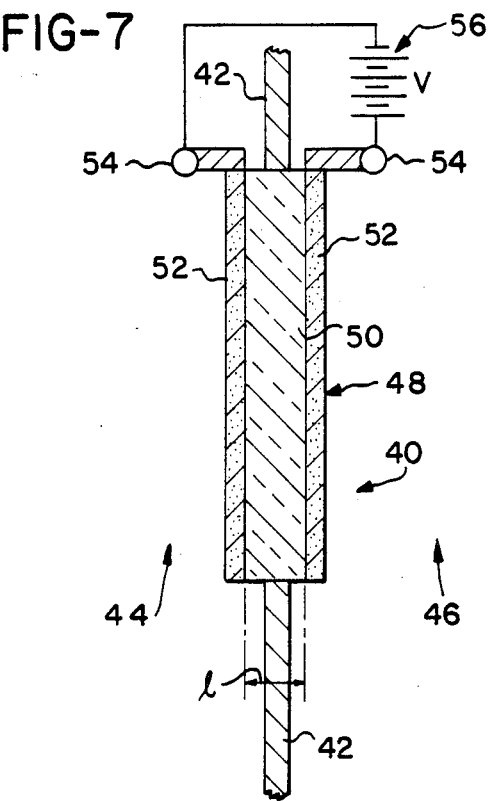
FIG. 7 is a schematic representation of an exemplary oxygen separator embodiment.

The capabilities of an oxygen separator according to the present invention can be better appreciated by considering the exemplary oxygen separator shown in FIG. 7. A single layer separator 40 is mounted into a baffle 42 disposed so as to maintain air on a first side of baffle 42 indicated generally at 44 and a vacuum on the opposite side indicated generally at 46. The separator 40 includes a body 48 having a layer 50 of an electrolytic ceramic material covered by porous layers 52 of a metallic material. Electrodes 54 are connected to each metallic layer 52, and a voltage source 56 is connected between electrodes 54.

Separator 40 may also be exposed on one side (i.e., at 44) to contaminated air or some other gas having an oxygen partial pressure. By driving oxygen ions across layer 50 to fill an evacuated space or enrich the oxygen content of a second gas, a filtration effect can be produced.

As indicated in FIG. 7, source 56 applies a voltage V and ceramic layer 50 is of a thickness l. Assuming that the current I across the ceramic layer 50 is due entirely to movement of oxygen ions (i.e, any electronic conduction is negligible), the mass m of oxygen transported is $$m = IM\Delta t/zeN_o \quad (5)$$

where M is the molecular weight (16 g for oxygen ions), $\Delta t$ is the time interval in seconds, z is the ionic charge, e is the charge on a single electron, and $N_o$ is Avogadro's number. Substituting and making the appropriate units conversion, $$m = (8.29 \times 10^{-5})It. \quad (6)$$

where m is in grams, I is in amperes and t is in seconds. Substituting from Coulomb's law for I, $$m = (8.29 \times 10^{-5})Vt\sigma A/l \quad (7)$$

where V is the applied voltage, $\sigma$ is the ionic conductivity, and A is the exposed area (through porous metallic layers 52) of ceramic layer 50.

Taking as an example the $Bi_2O_3:Nb_2O_5$ ceramic material, the $\sigma T$ data presented in FIG. 6 enables $\sigma$ to be found as a function of T. For purposes of example, it will be assumed that $l = 0.005'' = 1.27 \times 10^{-2}$ cm, V = 500 volts, and A = $10^3$ cm$^2$ (i.e., approximately 1 sq. ft.). Then in one hour the following amounts of oxygen will be passed through ceramic layer 50:

TABLE II

| T (°C.) | Mass of Oxygen Transported Mass of Oxygen Transported Per Hour |
|---|---|
| 400 | $1.572 \times 10^4$ g = 34.6 lb. |
| 500 | $1.275 \times 10^5$ g = 280.7 lb. |
| 600 | $6.305 \times 10^5$ g = 1389 lb. = 0.69 tons |

Thus, in a 24 hour period, the exemplary separator 40 operating at 600° C. could transport about 17 tons of oxygen into an evacuated space.

From a practical point of view, the need to heat an oxygen separator to approximately 500° to 600° C. requires such an expenditure of energy that the efficiency of the separator may be a substantial drawback compared to other large scale oxygen separation devices. However, the present invention can be quite useful in applications where efficiency is not as important as convenience, or applications where waste heat is readily available.

While the forms of apparatus and the methods herein described constitute preferred embodiments of this invention, it is to be understood that the invention is not limited to these precise forms of apparatus and methods, and that changes may be made therein without departing from the scope of the invention which is defined in the appended claims.

What is claimed is:

1. An oxygen separator for separating oxygen from a first gas, comprising:
   at least two layers of a porous metallic conductor;
   at least one layer of an electrolytic ceramic material $Ni(Nb_{1-x}M_x)_2O_{6-x}$ wherein M is selected from the group consising of $Zr^{+4}$ and $Ti^{+4}$, $Sn^{+4}$, $Sm^{+4}$, $Hf^{+4}$, $Ce^{+4}$ and mixtures thereof, and wherein x is from 0 to 0.2;
   said ceramic layer being disposed between said metallic layers and cooperating therewith to form at least a portion of a body for said separator; and
   a voltage source connected between said metallic layers.

2. The separator of claim 1 in which said ceramic material comprises $NiNb_2O_6$.

3. The separator of claim 1 wherein said porous metallic conductor is platinum.

4. The separator of claim 1, further comprising:
   a first electrode connected to a first of said layers of said porous metallic conductor; and
   a second electrode connected to a second of said layers of said porous metallic conductor;
   said voltage source being connected between said metallic layers by connection with said first and second electrodes.

5. An oxygen separator for separating oxygen from a first gas, comprising:
   at least two layers of a porous metallic conductor;
   at least one layer of an electrolytic ceramic material $Ni_2(Nb_{1-x}M_x)_2O_{7-x}$ wherein M is selected from the group consisting of $Zr^{+4}$ $Ti^{+4}$, $Sn^{+4}$, $Sm^{+4}$, $Hf^{+4}$, $Ce^{+4}$ and mixtures thereof, and wherein x is from 0 to 0.2;
   said layer of ceramic material being disposed between said layers of said porous metallic conductor and cooperating therewith to form at leat a portion of a body for said separator; and
   a voltage source connected between said metallic layers.

6. The separator of claim 5 wherein said porous metallic conductor is platinum.

7. The separator of claim 5, further comprising:
   a first electrode connected to a first of said layers of said porous metallic conductor; and
   a second electrode connected to a second of said layers of said porous metallic conductor;
   said voltage source being connected between said metallic layers by connection with said first and second electrodes.

* * * * *